(12) United States Patent
Ohta et al.

(10) Patent No.: US 6,184,008 B1
(45) Date of Patent: Feb. 6, 2001

(54) PRODUCTION OF OPTICALLY ACTIVE SPHINGOID COMPOUND

(75) Inventors: Hiromichi Ohta, Tokyo; Takeshi Sugai, Yokohama; Takeshi Ishii; Satoshi Mitsuda, both of Takarazuka, all of (JP)

(73) Assignee: Sumitomo Chemical Company Ltd., Osaka (JP)

( * ) Notice: Under 35 U.S.C. 154(b), the term of this patent shall be extended for 0 days.

(21) Appl. No.: 09/336,601

(22) Filed: Jun. 21, 1999

Related U.S. Application Data

(62) Division of application No. 09/034,007, filed on Mar. 3, 1998, now abandoned.

(30) Foreign Application Priority Data

Mar. 3, 1997 (JP) ...................................... 9/047840

(51) Int. Cl.[7] .............................. C12P 13/02; C12P 41/00
(52) U.S. Cl. ....................... 435/129; 435/195; 435/197; 435/280
(58) Field of Search .................................. 435/129, 195, 435/197, 280

(56) References Cited

U.S. PATENT DOCUMENTS

| | | |
|---|---|---|
| 4,607,013 | 8/1986 | Mitsuda et al. . |
| 5,290,694 | 3/1994 | Nakanishi et al. . |
| 5,306,636 | 4/1994 | Iizumi et al. . |

FOREIGN PATENT DOCUMENTS

| | | |
|---|---|---|
| 0146810A2 | 7/1985 | (EP) . |
| 0189878A2 | 8/1986 | (EP) . |
| 0487541B1 | 6/1992 | (EP) . |
| 0657535A2 | 6/1995 | (EP) . |
| 0472336A1 | 2/1996 | (EP) . |
| 06153965A | 11/1992 | (JP) . |
| 680617A | 3/1994 | (JP) . |
| 9313200 | 7/1993 | (WO) . |
| WO9534525A1 | 12/1995 | (WO) . |

OTHER PUBLICATIONS

Jorgensen et al., Journal of Bacteriology, vol. 173, No. 2, 559–567 (1991).
Hirose et al., Tetrahedron, vol. 36, No. 7, 1063–1066 (1995).
Sugihara et al., J. Biochem. 112, 598–603 (1992).
Sih et al., Tetrahedron, vol. 6, No. 2, 357–360 (1995).
Kinoshita et al., Tetrahedron, vol. 52, No. 15, 5397–5406 (1996).
Frenken et al., Applied and Environmental Microbiology, vol. 58, No. 12, 3787–3791 (1992).
Schrag et al., Structure, vol. 5, No. 2, 187–202 (1997).
Julina et al., *Helvetica Chimica Acta,* vol. 69, pp. 368–373 (1986).
Shibuya et al., *Tetrahedron Letters,* vol. 30, No. 51, pp. 7205–7208 (1989).
Nicolaou et al., *J. Am. Chem. Soc.,* vol. 110, pp. 7910–7912 (1988).
Abe et al., *J. Biol. Chem.,* vol. 271, No. 24, pp. 14383–14389 (1996).

*Primary Examiner*—Herbert J. Lilling
(74) *Attorney, Agent, or Firm*—Birch, Stewart, Kolasch & Birch, LLP

(57) ABSTRACT

An industrially advantageous production method of an optically active alcohol useful for cosmetics and medical supplies or production intermediates thereof using an esterase having an ability to selectively hydrolyze an optically active sphingoid compound.

4 Claims, No Drawings

SEQUENCE LISTING

<160> NUMBER OF SEQ ID NOS: 2

<210> SEQ ID NO 1
<211> LENGTH: 363
<212> TYPE: PRT
<213> ORGANISM: E. coli JM 109/pAL 612 strain

<400> SEQUENCE: 1

```
Met Ser Arg Ser Ile Arg Ala Lys Ala Val Ala Thr Val Val Ala Ile
 1               5                  10                  15

Ala Met Asn Ala Ala Pro Ala Ala Ser Val Gly Thr Val Leu Ser Leu
                20                  25                  30

Ala Gly Ala Gln Ala Ala Ser Ala Ala Thr Thr Ala Val Asp Asp Tyr
            35                  40                  45

Ala Ala Thr Arg Tyr Pro Ile Ile Leu Val His Gly Leu Thr Gly Thr
        50                  55                  60

Asp Lys Tyr Gly Gly Val Val Glu Tyr Trp Tyr Arg Ile Pro Glu Asp
65                  70                  75                  80

Leu Arg Ala His Gly Ala Ala Val Tyr Val Ala Asn Leu Ser Gly Phe
                85                  90                  95

Gln Ser Asp Asp Gly Pro Asn Gly Arg Gly Glu Gln Leu Leu Ala Phe
            100                 105                 110

Val Lys Gln Val Leu Ala Ala Thr Gly Ala Gln Lys Val Asn Leu Ile
        115                 120                 125

Gly His Ser Gln Gly Gly Leu Thr Ser Arg Tyr Val Ala Ser Val Ala
    130                 135                 140

Pro Glu Leu Val Ala Ser Val Thr Thr Ile Ser Thr Pro His Trp Gly
145                 150                 155                 160

Ser Gln Phe Ala Asp Phe Val Gln Gln Leu Leu Gln Thr Asp Pro Thr
                165                 170                 175

Gly Leu Ser Ser Thr Val Leu Gly Ala Phe Ala Asn Ala Leu Gly Thr
            180                 185                 190

Leu Thr Ser Ser Asn Phe Asn Thr Asn Gln Asn Ala Ile Gln Ala Leu
        195                 200                 205

Ser Val Leu Thr Thr Ala Lys Ala Ala Ala Tyr Asn Gln Lys Phe Pro
    210                 215                 220

Ser Ala Gly Leu Gly Ala Pro Gly Ser Cys Gln Thr Gly Ala Pro Thr
225                 230                 235                 240

Glu Thr Val Gly Gly Asn Thr His Leu Leu Tyr Ser Trp Gly Gly Thr
                245                 250                 255

Ala Ile Gln Pro Thr Ala Thr Val Ala Gly Val Thr Gly Ala Val Asp
            260                 265                 270

Thr Ser Val Ser Gly Val Thr Asp Pro Ala Asn Ala Leu Asp Pro Ser
        275                 280                 285

Thr Leu Ala Leu Leu Gly Ser Gly Thr Val Met Ile Asn Arg Ser Ala
    290                 295                 300

Gly Pro Asn Asp Gly Val Val Ser Gln Cys Ser Ala Arg Phe Gly Gln
305                 310                 315                 320

Val Leu Gly Thr Tyr His Trp Asn His Thr Asp Ala Ile Asn Gln Ile
                325                 330                 335

Leu Gly Val Leu Gly Ala Asn Val Glu Asp Pro Val Ala Val Ile Arg
            340                 345                 350

Thr His Ala Asn Arg Leu Lys Asn Gln Gly Val
```

```
                   355              360

<210> SEQ ID NO 2
<211> LENGTH: 1089
<212> TYPE: DNA
<213> ORGANISM: E. coli JM 109/pAL 612 strain

<400> SEQUENCE: 2
atgagcagat cgatacgagc gaaggcagtg gcgaccgtgg tggcgatcaa cgcggccccg     60
gccgcgagtg ttggaaccgt tctggccatg tcgctggccg gcgcacaggc cgcttccgcc    120
gcgacgaccg ccgttgacga ctacgcggcg acccggtacc cgatcattct cgtgcacggg    180
ctgaccggca ccgacaagta cggtggcgtc gtcgagtact ggtatcgcat tccggaggac    240
ctgcgggcgc acggcgcggc ggtatacgtt gccaacctgt ccggcttcca gagcgacgat    300
ggcccgaacg ggcgtggcga gcaattgctt gcattcgtga agcaggtgct cgcggcgacg    360
ggcgcgcaga aggtgaatct gatcggccat agccagggcg gcctgacatc gcgttatgtt    420
gcgtccgttg caccggaact ggtcgcatcg gtgacgacga tcagtacgcc gcactggggc    480
tcgcaattcg cggacttcgt ccagcaactg ttgcagacgg acccgaccgg cctgtcgtcg    540
accgtgctcg gcgcattcgc gaatgcgctc ggcacgttga cgagcagcaa cttcaatacg    600
aaccagaatg cgattcaggc gttgtcggtg ctgacgacgg caaggccgc cgcatacaac     660 cagaaattcc cgagcgccgg tctcggtgcg ccgggctcgt gtcaaaccgg cgcgccaacg    720
gagactgtcg gcggcaatac gcatctgctt tattcgtggg gcggcacggc gatccagccg    780
acagcgacgg tggccggcgt gacaggggcc gtcgatacga gcgtgagcgg ggtcaccgat    840
ccggcgaacg cgctcgatcc gtcaacgctg gcactcctcg gcagcggcac ggtgatgatc    900
aatcgcagcg ccggtccgaa cgatggcgtc gtgtcgcaat gcagcgcgcg gtttggccag    960
gtgctcggca cgtatcactg gaatcacacc gatgcgatca accagatcct cggcgtgctc   1020
ggcgcgaatg tggaggatcc ggttgcggta atccgcacgc acgcgaaccg gttgaagaat   1080
caaggcgtg                                                           1089
```

PRODUCTION OF OPTICALLY ACTIVE SPHINGOID COMPOUND

This application is a divisional of application No. 09/034,007, filed on Mar. 3, 1998, now abandoned the entire contents of which are hereby incorporated by reference.

BACKGROUND OF THE INVENTION

1. Field of the Invention

The present invention relates to a method for producing an optically active sphingoid compound.

2. Description of the Related Art

Optically active sphingoid compounds having optically active erythro amino alcohol moiety have been used in cosmetics and medical supplies for treatment of hair and skin or production intermediates thereof.

Conventionally, these compounds are extracted and separated mainly from epidermis tissue of animals such as cows and pigs, alternatively obtained by several synthetic steps. However, they are expensive and a stable supply thereof is difficult since the production amount is limited. Therefore, a further provision of a convenient method for producing the said compound has been desired.

SUMMARY OF THE INVENTION

An object of the present invention is to provide: a method for producing an optically active erythro sphingoid ester of the formula I:

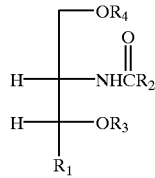

wherein $R_1$ and $R_2$ may be the same or different and represent an aliphatic hydrocarbon having 7 to 31 carbon atoms which may be substituted by one or more hydroxyl groups, and $R_3$ and $R_4$ may be the same or different and represent an acyl group having 1 to 7 carbon atoms, which comprises:

allowing a racemic mixture comprising the optically active erythro sphingoid ester of the formula I as defined above and its enantiomer to contact with an esterase having the ability to selectively hydrolyze the said enantiomer of the optically active erythro sphingoid ester of the formula I to produce an optically active erythro sphingoid alcohol compound of the formula II:

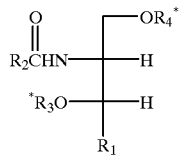

wherein $R_1$ and $R_2$ have the same meaning as defined above, and $R_3{}^*$, and $R_4{}^*$ represent a hydrogen atom and an acyl group having 1 to 7 carbon atoms provided that $R_3{}^*$ and $R_4{}^*$ do not simultaneously represent an acyl group having 1 to 7 carbon atoms; and recovering the optically active erythro sphingoid ester of the formula I.

DESCRIPTION OF THE PREFERRED EMBODIMENT

Next, a description will be made to the racemic mixture comprising the optically active erythro sphingoid ester compound of the formula I as defined above and its enantiomer represented by the formula II as defined above.

Examples of the aliphatic hydrocarbon having 7 to 31 carbon atoms which may he substituted by one or more hydroxyl groups, represented by $R_1$ and $R_2$, for example, include:

a liner or branched alkyl group having 7 to 31 carbon atoms which may be substituted by one or more hydroxyl groups, a liner or branched alkenyl group having 7 to 31 carbon atoms which has one or more double bonds and may be substituted by one or more hydroxyl groups, and the like.

A liner or branched alkyl group having 7 to 31 carbon atoms which may be substituted by one to three hydroxyl groups, a liner or branched alkenyl group having 7 to 31 carbon atoms which has one to three double bonds and may be substituted by one to three hydroxyl groups and the like, are preferred.

Among the aliphatic hydrocarbon having 7 to 31 carbon atoms which may be substituted by one or more hydroxyl groups, for $R_1$ and $R_2$, the aliphatic hydrocarbon having 7 to 26 carbon atoms which may be substitiuted by one or more hydroxyl groups are preferred.

Specific examples of the above-described preferred alkyl or alkenyl groups include:

a heptyl group, tridecyl group, tetradecyl group, pentadecenyl group, hexadecyl group, heptadecyl group, octadecyl group, nonadecyl group, eicosyl group, heneicosyl group, docosyl group, tricosyl group, tetracosyl group, pentacosyl group, hexacosyl group, heptacosyl group, octacosyl group, nonacosyl group, tracontyl group, hentriacontyl group, 1-tridecenyl group, 1-tetradecenyl group, 1-pentadecenyl group, 1-hexadecenyl group, 1-heptadecenyl group, 1-octadecenyl group, 1-nonadecenyl group, 1-eicosenyl group, 1-hydroxytetradecyl group, 1-hydroxypentadecyl group, 1-hydroxthexadecyl group, 1-hydroxtheptadecyl group, 1-hydroxyoctadecyl group, 1-hydroxynondecyl group, 1-hydroxyeicosyl group, 1-hydroxtheneicosyl group, 1-hydroxydocosyl groun, 1-hydroxytricosyl group, 1-hydroxytetracosyl group, 1-hydroxypentacosyl group, 1-hydroxyhexacosyl group, 1-hydroxyheptacosyl group, 12-methyl-tridecyl group, 14-methy-1-pentadecenyl group, 14-methyl-heptadecyl group and the like Examples of the acyl group having 1 to 7 carbon atoms for $R_3$ and $R_4$ include an alkylcarbonyl group having 2 to 7 carbon atoms and the like.

Specific examples of the acyl group include an acetyl group, propionyl group, butyryl group and the like.

An acetyl group is more preferred.

Specific examples of the racemic erythro sphingoid ester include:

N-heptadecanoyl-1,3-O,O-diacetyl-2-amino-4-hexadecene-1,3-diol,

N-heptadecanoyl-1,3-O,O-diacetyl-2-aminohexadecane-1,3-diol,

N-heptadecanoyl-1,3-O,O-diacetyl-2-amino-4-octadecene-1,3-diol,

N-heptadecanoyl-1,3-O,O-diacetyl-2-aminooctadecane-1,3,4-triol,
N-heptadecanoyl-1,3-O,O-diacetyl-2-aminoeicosane-1,3-diol,
N-heptadecanoyl-1,3-O,O-dibutyryl-2-aminoeicosane-1,3-diol,
N-heptadecanoyl-1,3-O,O-diacetyl-2-aminoheptacosane-1,3-diol,
N-octadecanoyl-1,3-O,O-diacetyl-2-amino-15-methylhexadecane-1,3-diol,
N-octadecanoyl-1,3-O,O-diacetyl-2-aminohexadecane-1,3-diol,
N-octadecanoyl-1,3-O,O-dibutyryl-2-aminohexadecane-1,3-diol,
N-octadecanoyl-1,3-O,O-diacetyl-2-amino-4-octadecence-1,3-diol,
N-octadecanoyl-1,3-O,O-diacetyl-2-aminooctadecane-1,3,4-triol,
N-octadecanoyl-1,3-O,O-diacetyl-2-aminoeicosane-1,3-diol,
N-octadecanoyl-1,3-O,O-dibutyryl-2-aminoheptacosane-1,3-diol,
N-2'-hydroxyoctadecanoyl-1,3-O,O-diacetyl-2-amino-15-methylhexadecane-1,3-diol,
N-2'-hydroxyhexadecanoyl-1,3-O,O-diacetyl-2-aminohexadecane-1,3-diol,
N-2'-hydroxyhexadecanoyl-1,3-O,O-dibutyryl-2-aminohexadecane-1,3-diol,
N-2'-hydroxyeicosanoyl-1,3-O,O-diacetyl-2-amino-4-octadecene-1,3-diol,
N-2'-hydroxyeicosanoyl-1,3-O,O-diacetyl-2-aminooctadecane-1,3,4-triol,
N-2'-hydroxytetracosanoyl-1,3-O,O-diacetyl-2-aminoeicosane-1,3-diol,
N-2'-hydroxyhexacosanoyl-1,3-O,O-dibutyryl-2-aminoheptacosane-1,3-diol,
N-docosanoyl-1,3-O,O-dibutyryl-2-amino-15-methyhexadecane-1,3-diol,
N-tetracosanoyl-1,3-O,O-diacetyl-2-aminohexadecane-1,3-diol,
N-hexacosanoyl-1,3-O,O-dibutyryl-2-aminohexadecane-1,3-diol,
N-methyloctadecanoyl-1,3-O,O-diacetyl-2-amino-4-octadecene-1,3-diol,
N-pentacosanoyl-1,3-O,O-diacetyl-2-amino-4-docosene-1,3-diol,
N-pentacosanoyl-1,3-O,O-diacetyl-2-amino-4-octadecene-1,3-diol,
N-pentacosanoyl-1,3-O,O-diacetyl-2-aminoeicosane-1,3-diol, and the like. These sphingoid esters can be obtained, for example, by a method disclosed by T. Kolter et al. (Tetrahedron, 50, p.13425(1994)).

The esterase includes an esterase, protease and the like in addition to a narrowly-defined lipase, and may be derived from animals such as hogs, human and the like, derived from plants such as ricinus and the like, or derived from microorganisms belonging to Aspergillus, Candida, Fusarium, Geotrichum, Mucor, Nocardia, Penicillium, Rhizopus, Saccharomyces, Acromobacter, Acinetobacter, Alcaligenes, Chromobacterium, Escherichia, Pseudomonas, Sphingomonas, Bacillus, Burkholderia, Moraxella, Lactobacillus, Staphylococcus, Serratia, Yarrowia and the like.

An esterase produced by a transformed host organism, into which an isolated gene of the esterase is introduced by using recombinant DNA technology, can be used in the present invention As the host organism, an organism belonging to the same genus or a host organism belonging to the different genus can be used.

As a more specific example of the esterase, a protein having an amino acid sequence represented by SEQUENCE ID NO: 2 or a sequence in which one or more amino acids in the amino acid sequence are added, deleted or substituted, is listed.

SEQ ID NO:1 represents the DNA sequence coding for the amino acid sequence represented by SEQ ID No:2.

A microorganism (*E. coli* JM 109/pAL 612 strain) producing the protein having the amino acid sequence represented by SEQUENCE ID NO: 2 has been deposited as FERM-BP5740 (accepted date: Nov. 7, 1996) under the Budapest Treaty at the Ministry of International Trade and Industry, Agency of Industrial Science and Technology, National Institute of Biochemical and Human-Technology.

The esterase may be used in the form of a microorganism containing the same or a cell culture, however, it may also be separated from the culture or tissue containing the esterase and utilized in the form of a crude enzyme, purified enzyme and the like, if necessary.

These crude enzyme, purified enzyme and the like can be prepared by a conventional method such as, for example,
(1) ultrasonic treatment,
(2) grinding treatment using glass beads or alumina,
(3) French press treatment,
(4) treatment with an enzyme such as lysozyme and the like,
(5) bacteria, cell, tissue or the like is ground by Warinq blender treatment and the like,
(6) the resulted ground material is salted out using ammonium sulfate and the like,
(7) precipitation by an organic solvent or an organic polymer such as polyethylene glycol and the like,
(8) various chromatographies such as ion exchange chromatography, hydrophobic chromatography, gel filtration chromatography, affinity chromatography and the like, and
(9) electrophoresis and the like.

The esterase may be insolubilized by a immobilization such as a carrier binding method in which the esterase is bound to a carrier by a covalent bond, ion bond, adsorption and the like, an entrapment method ir which the esterase is confined in gel structure.

The reaction is usually carried out from about 20° C. to about 70° C., preferably from about 25° C. to about 40° C. The reaction is preferably conducted in a two-layer system comprising an organic solvent which dissolves the sphingoid ester compound of the formula I as defined above and its enantiomer and a buffer solution which dissolves tile above-described esterase.

Examples of the organic solvent include, for example, decane and the like.

Examples of the buffer solution include a usual buffer solution having pH of about 5 to about 8.

The reaction time can be optionally set, for example, from about 1 hour to about 1 week.

For recovery of the optically active erythro sphingoid ester of the formula I from the reaction solution, conventional methods such as, for example, solvent extraction, fractional distillation, column chromatography and the like may be used, and optionally, these methods may also be appropriately combined for use, if necessary.

The optically active erythro sphingoid ester of the formula I as defined above can be allowed to react with either an acid or a base to effect a hydrolysis reaction by a conventional method to obtain an optically active erythro sphingoid alcohol of the formula I':

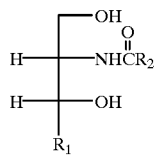

wherein $R_1$ and $R_2$ are the same as defined for the formula I above.

Examples of thus obtained optically active erythro sphingoid alcohols includes optically active erythro isomers of the following compounds such as:
N-heptadecanoyl-2-amino-4-hexadecene-1,3-diol,
N-heptadecanoyl-2-aminohexadecane-1,3-diol,
N-heptadecanoyl-2-amino-4-octadecene-1,3-diol,
N-heptadecanoyl-2-aminooctadecane-1,3,4-triol,
N-heptadecanoyl-2-aminoeicosane-1,3-diol,
N-heptadecanoyl-2-aminoeicosane-1,3-diol,
N-heptadecanoyl-2-aminoheptacosane-1,3-diol,
N-octadecanoyl-2-amino-15-methylhexadecane-1,3-diol,
N-octadecanoyl-2-aminohexadecane-1,3-diol,
N-octadecanoyl-2-amino-4-octadecene-1,3-diol,
N-octadecanoyl-2-aminooctadecane-1,3,4-triol,
N-octadecanoyl-2-aminoeicosane-1,3-diol,
N-octadecanoyl-2-aminoheptacosane-1,3-diol,
N-2'-hydroxyoctadecanoyl-2-amino-15-methylhexadecane-1,3-diol,
N-2'-hydroxyhexadecanoyl-2-aminohexadecane-1,3-diol,
N-2'-hydroxyeicosanoyl-2-amino-4-octadecene-1,3-diol,
N-2'-hydroxyeicosanoyl-2-aminooctadecane-1,3,4-triol,
N-2'-hydroxytetracosanoyl-2-aminoeicosane-1,3-diol,
N-2'-hydroxyhexaconoyl-2-aminoheptacosane-1,3-diol,
N-docosanoyl-2-amino-15-methyhexadecane-1,3-diol,
N-tetracosanoyl-2-aminohexadecane-1,3-diol,
N-hexacosanoyl-2-aminohexadecane-1,3-diol,
N-methyloctadecanoyl-2-amino-4-octadecene-1,3-diol,
N-pentacosanoyl-2-amino-4-docosene-1,3-diol,
N-pentacosanoyl-2-amino-4-octadecene-1,3-diol,
N-pentacosanoyl-2-aminoeicosane-1,3-diol, and the like.

EXAMPLE

The following examples further illustrate the present invention in detail, but they are not to be construed to limit the scope thereof.

Example 1

To a mixed solution of 10 ml decane and 100 ml of a phosphate buffer solution were added 1.03 g of racemic erythro-3-acetoxy-2-stearoylaminohexadecyl acetate and 50 mg of an esterase prepared in Reference Example 1 below, and the resulted mixture was reacted by stirring at 30° C. The reaction was traced by TLC [silica gel, hexane:ethyl acetate (2:1), chloroform:methanol (15:1)].

The reaction was continued for 2 days, and then, the reaction solution was diluted with ethyl acetate, and then extracted with chloroform. The recovered organic solvent layer was washed with salt water, then, dried over anhydrous sodium sulfate, and the filtered solution was concentrated under reduced pressure to obtain a residue. The resulted residue was separated by silica gel column chromatography using hexane:ethyl acetate (5:1) and chloroform:methanol (30:1) as eluent. A sample of the eluted (+)-(2S,3R)erythro-3-acetoxy-2-stearoylaminohexadecyl acetate (264.9 mg) was hydrolyzed, then converted to (4R,5S)-erythro-2,2-dimethyl-5-stearoylamino-4-tridecyl-1,3-dioxane in the presence of p-toluenesulfonic acid, 2,2-dimethoxypropane and acetone, and the optical purity was analyzed by $^1$H-NMR to find it was >95%e.e.

Then, a sample of the elated (−)-(2R,3S)-3-acetoxy-2-stearoylaminohexadecane-1-ol (481.8 mg) was hydrolyzed, and compared with angle of rotation of (−)-(2R,3S)-erythro-2-stearoylamino-1,3-hexadecanediol, to find a optical purity of 16%e.e Then, a part of the eluted (−)-(2R,3S)-erythro-2-stearoylamino-1,3-hexanediol (214.8 mg) was converted to (4S,5R)-erythro-2,2-dimethyl-5-stearoylamino-4-tridecyl-1,3-dioxane according to the method as described above. The optical purity was analyzed by $^1$H-NMR to find it was >95%e.e.

Example 2

To a mixed solution of 10 ml decane and 100 ml of a phosphate buffer solution were added 10.2 mg of racemic erythro-3-acetoxy-2-stearoylaminohexadecyl acetate and 10.8 mg of an immobolized esterase prepared in Reference Example 2 below, and the resulted mixture reacted under stirring at 30° C. The reaction was traced by TLC [silica gel, hexane:ethyl acetate (2:1), chloroform:methanol (15:1)].

The reaction was continued for 2 days, and then, the product (+)-(2S,3R)-erythro-3-acetoxy-2-stearoylaminohexadecyl acetate was separated according to the method described in Example 1.

Then a sample of the-separated product was hydrolyzed, then reacted with α-methoxy-α-trifluoromethylphenyl acetate (hereinafter, referred to as MTPA), converted to a bis-MTPA ester, then, optical purity was analyzed by $^1$H-NMR.

(+)-(2S, 3R) -erythro-2-acetoxy-2-stearoylaminohexadecyl acetate was obtained in a yield of 50%, and the optical purity was >95%e.e.

Reference Example 1

Preparation of Esterase

Recombinant *E. coli* JM109/pAL612 strain (FREM-BP 5740) was incubated in 100 ml of a LB medium (manufactured by Difco) containing 50 mg/L of ampicillin and 1 mM of isopropyl thio-β-D-galactoside, at 37° C. for 16 hours, then the culture was subjected to centrifuged (6000 rpm, 10 minutes) to recover microorganism The recovered microorganism was suspended i n a 10 ml of 100 mM phosphate buffer solution (pH 7.0), then was broken by ultrasonic wave, and the broken material was centrifuged to obtain a crude enzyme extract solution. Then, the resulted crude enzyme extract solution was freeze-dried to obtain a crude enzyme powder.

Reference Example 2

Immobilization of Esterase

To a 10 ml of 0.1 M phosphate buffer solution (pH 7.0) into which Triton X-100 (TRM of Union Carbide Chemicals and Plastics) (300 mg) was dissolved was added 1 g of the enzyme powder obtained in Reference Example 1, then, Florysil (TRM of U.S. Silica Company, purchased from Aldrich Japan) (8.7 mg) was added in ice water. The resulted mixture was frozen at −78° C. then freeze-dried to obtain 1.4 g of an immobilized powdery enzyme.

What is claimed is:

1. A method for producing an optically active erythro sphingoid ester of the formula I:

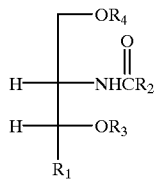

wherein $R_1$ and $R_2$, may be the same or different, represent an aliphatic hydrocarbon having 7 to 31 carbon atoms which may be substituted by one or more hydroxyl groups, and
$R_3$ and $R_4$ may be the same or different and represent an acyl group having 1 to 7 carbon atoms,
which comprises:
allowing a racemic mixture comprising the optically active sphingoid ester of the formula I as defined above and its enantiomer to contact with an esterase having an ability to selectively hydrolyze the said enantiomer of the optically active sphingoid ester of the formula I to produce an optically active sphingoid alcohol compound of the formula II:

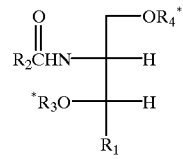

wherein $R_1$ and $R_2$ have the same meaning as defined above, and $R_3^*$, and $R_4^*$ represent a hydrogen atom and an acyl group having to 7 carbon atoms provide that $R_3^*$, and $R_4^*$ do not simultaneously represent an acyl group having 1 to 6 carbon atoms; and recovering the optically active erythro sphingoid ester of the formula I.

2. A method for producing an optically active erythro sphingoid alcohol of the formula I':

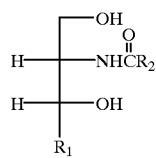

wherein $R_1$ and $R_2$ are the same as defined in claim 1, which comprises:

allowing the recovered optically active erythro sphingoid ester of the formula I as defined in claim 1 to hydrolysis reaction.

3. The method according to claim 1, wherein the esterase is a protein having an amino acid sequence of SEQUENCE ID NO: 2.

4. The method according to claim 2, wherein the esterase is a protein having an amino acid sequence of SEQUENCE ID NO: 2.

* * * * *